(12) United States Patent
Karl (10) Patent No.: US 11,484,411 B2
(45) Date of Patent: Nov. 1, 2022

(54) JOINT IMPLANT FOR NEW TISSUE FORMATION AT THE JOINT

(71) Applicant: Christoph Karl, Kreuzlingen (CH)

(72) Inventor: Christoph Karl, Kreuzlingen (CH)

(*) Notice: Subject to any disclaimer, the term of this patent is extended or adjusted under 35 U.S.C. 154(b) by 0 days.

(21) Appl. No.: 16/466,174

(22) PCT Filed: Oct. 19, 2017

(86) PCT No.: PCT/EP2017/076691
§ 371 (c)(1),
(2) Date: Jun. 3, 2019

(87) PCT Pub. No.: WO2018/108360
PCT Pub. Date: Jun. 21, 2018

(65) Prior Publication Data
US 2019/0290440 A1  Sep. 26, 2019

(30) Foreign Application Priority Data

Dec. 12, 2016  (DE) ..................... 10 2016 124 049.4

(51) Int. Cl.
*A61F 2/30* (2006.01)
*A61F 2/28* (2006.01)

(52) U.S. Cl.
CPC ............ *A61F 2/30756* (2013.01); *A61F 2/28* (2013.01); *A61F 2/30942* (2013.01); *A61F 2002/30031* (2013.01); *A61F 2002/3084* (2013.01); *A61F 2002/3092* (2013.01); *A61F 2002/30766* (2013.01); *A61F 2002/30943* (2013.01); *A61F 2002/30962* (2013.01); *A61F 2002/30985* (2013.01)

(58) Field of Classification Search
CPC ................... A61F 2/30756; A61F 2/28; A61F 2002/30031; A61F 2002/30766; A61F 2002/3084
See application file for complete search history.

(56) References Cited

U.S. PATENT DOCUMENTS

| | | | |
|---|---|---|---|
| 6,319,712 B1 | 11/2001 | Meenen | |
| 6,660,363 B1 | 12/2003 | Barthlott | |
| 7,217,294 B2 | 5/2007 | Kusanagi | |
| 10,196,610 B2 | 2/2019 | Kato | |
| 2003/0006534 A1* | 1/2003 | Taboas | ................ A61F 2/30756 264/401 |
| 2005/0149046 A1 | 7/2005 | Friedman | |
| 2005/0221072 A1 | 10/2005 | Dubrow | |
| 2008/0249637 A1 | 10/2008 | Asgari | |

(Continued)

FOREIGN PATENT DOCUMENTS

| | | |
|---|---|---|
| CN | 104645419 | 5/2015 |
| EP | 2465549 | 6/2012 |

(Continued)

*Primary Examiner* — Jennifer Dieterle
*Assistant Examiner* — Rebecca Lynee Zimmerman
(74) *Attorney, Agent, or Firm* — Duane Morris LLP; Gregory M. Lefkowitz; Brandon A. Chan (57) ABSTRACT

The invention relates to a joint implant for new tissue formation at a joint, the joint implant (1) comprising a pinlike body having a bottom region (11), a top region (12) and a shell region (13), wherein at least the top region (12), of the joint implant (1) has a hydrophobic surface for promoting chondroblastic differentiation of mesenchymal stem cells.

17 Claims, 8 Drawing Sheets

(56) References Cited

U.S. PATENT DOCUMENTS

| | | | | |
|---|---|---|---|---|
| 2009/0029077 | A1* | 1/2009 | Atanasoska | A61L 31/146 428/34.1 |
| 2012/0177702 | A1* | 7/2012 | Altschuler | A61F 2/28 424/400 |
| 2014/0200679 | A1* | 7/2014 | Bluecher | A61F 2/0063 623/23.74 |
| 2014/0324169 | A1* | 10/2014 | Maher | A61L 27/18 623/14.12 |
| 2016/0318247 | A1* | 11/2016 | Schlachter | B33Y 10/00 |
| 2016/0331869 | A1 | 11/2016 | Biris | |
| 2017/0281829 | A1* | 10/2017 | Biris | A61L 27/38 |
| 2019/0083282 | A1* | 3/2019 | Roeder | A61L 27/54 |

FOREIGN PATENT DOCUMENTS

| | | |
|---|---|---|
| WO | 03/045463 | 6/2003 |
| WO | 2007/020449 | 2/2007 |
| WO | 2012/096997 | 7/2012 |

* cited by examiner

JOINT IMPLANT FOR NEW TISSUE FORMATION AT THE JOINT

CROSS-REFERENCE TO RELATED APPLICATIONS

This application is a § 371 national stage entry of International Application No. PCT/EP2017/076691, filed on Oct. 19, 2017, which claims priority to German Patent Application No. 10 2016 124 049.4, filed on Dec. 12, 2016, the entire contents of which are incorporated herein by reference.

The present invention pertains to a joint implant for new tissue formation at the joint, and more particularly to a joint implant for new cartilage formation at the knee, hip, shoulder, ankle, metatarsophalangeal or wrist joint.

Joint disorders (arthritis) are among the ten most frequent disorders worldwide. Completely replacing the disordered joint entails high costs and is commonly perceived by the patients affected to be mentally stressful. Revisions of the joint prosthesis involve further costs, stresses for the patient, and, often, complications. Various approaches have therefore been developed to the curative treatment of joint disorders (arthritis), and especially to the curative treatment of knee and hip joint arthritis.

The approaches currently in existence to the curative treatment of joint disorders are explained below.

Drug therapy options: The drug therapy options are confined to the symptomatic administration of antiinflammatories and painkillers and also to the partially intraarticular and partially systemic treatment with hyaluronic acid, chondroitin sulphate, interleukin-1 receptor antagonists and glucosamine sulphate. Despite good results having been demonstrated here in reducing pain, it has not so far been possible by this means to prevent the progression of the arthritis.

Surgical therapies: Surgical therapies as well, such as local bone or cartilage transplant and/or autologous chondrocyte transplant or implant (ACT or ACI), have failed so far to establish themselves, requiring as they do two operations (removal and reimplantation), thus implying long resting or immobilization of the joint during rehabilitation, with consequent detrimental effects on regeneration. At the site of removal, moreover, the cartilage that is still healthy is damaged.

The most widespread therapies are therefore surgical therapies such as that known as Pridie drilling, anterograde/retrograde drilling, and microfracturing. These surgical therapies do not involve local replacement of cartilage; instead, for example, a number of holes are made through the subchondral border lamella. In the case of Pridie drilling and its onward development in the form of "microfracturing", blood can be made to enter the cartilage defect in the defect area, and so fibrocytes, mesenchymal stem cells and chondroblasts are carried from the spongiose compartment into the cartilage defect. Together with growth factors, these species form a blood coagulum ("super clot") and undergo differentiation into articular cartilage. Clinical studies have shown pain reduction and high joint mobility. A problem here as well, however, is long resting or immobilization of the joint, during which the regenerative quality of the fibrocartilage that develops is in general of low grade. Because of its structure, this fibrocartilage is often insufficient for the high mechanical loads, particularly in the knee joint, and undergoes rapid degeneration, which may necessitate further interventions.

For this reason, carbon pins have been developed as joint implants for new tissue formation at the joint, these pins being inserted into the drilled holes and being intended to lead to rapid overgrowth.

EP 1 450 875 A1 discloses a joint implant of this kind for new tissue formation at the joint, where the pins employed are made from compacted carbon having a predetermined porosity. When conventional carbon pins of this kind are used, as well, fibrocytes and mesenchymal stem cells can be carried from the spongiose compartment into the cartilage defect, and they form a "super clot" and undergo differentiation into articular cartilage.

The system has so far failed to establish itself, however, because of two key disadvantages. On the one hand, orthopaedic surgeons do not accept carbon as a material in the cartilage, fearing microabrasion. On the other hand, the surface is not designed for colonization by stem cells, a fact which here as well is manifested in a low-grade regenerative quality of the fibrocartilage developed.

Because of these limitations, none of the therapies stated above has been able to date to become the "standard of care".

It is an object of the invention, therefore, to provide a joint implant for new tissue formation at the joint that exhibits improved properties in the context of new tissue formation.

This object is achieved in accordance with the invention by the features of claim 1.

In particular through the use of a pinlike body wherein at least the top region of the joint implant has a hydrophobic surface, for the purpose of chondroblastic differentiation and hence of promoting the chondrogenesis of mesenchymal stem cells, it is possible to improve new tissue formation and, in particular, new cartilage formation at the joint, and also the formation of robust cartilage of relatively high quality. As a result of the use of the implant of the invention, moreover, long-lasting cartilage regeneration can be achieved, which is sustainable as a result of the ongoing transport of mesenchymal stem cells in the direction of the joint cavity, such regeneration allowing further interventions on the joint to be delayed or rendered unnecessary.

The pinlike body and in particular its top region are preferably produced by an artificial trabecular structure by means of a 3D printing process, thus allowing the construction, the perviosity and the sizing of the pinlike body to be defined with great precision.

The material of the pinlike body may, for example, comprise a non-bioabsorbable polymer, more particularly PA, PEK, PEKK, PEEK and UHMWPE, or a bioabsorbable polymer, e.g. PCL.

Alternatively, the material of the pinlike body may also comprise a metal, more particularly Ti, especially grade 1 pure titanium, stainless steel, or a metal alloy, more particularly Ti6Al4V (also called Ti64), especially CoCr, or a non-bioabsorbable ceramic, more particularly Al2O3, ZrO2, or a bioabsorbable ceramic, more particularly Ca3(PO4)2, hence allowing the realization of a joint implant having high mechanical strength and having improved properties of new tissue formation.

The hydrophobic surface may preferably be realized through a hydrophobic chemical coating on a hydrophilic porous substrate, thus allowing the chondroblastic differentiation to be realized with particular simplicity and effectiveness.

For example, the hydrophobic chemical coating comprises a segmented polymer, preferably a polyurethane or polyelectrolyte, or a hydrophobically functionalized chitosan or chitosan derivative.

The hydrophobic surface may further be realized through hydrophobic nanostructuring of a substrate, something which further promotes the chondroblastic differentiation of stem cells.

The pinlike body may preferably further comprise a coating, more particularly comprising a growth factor, thus further improving cartilage differentiation and also the growth of tissue and, in particular, of cartilage material on the joint implant and at the defect site.

Furthermore, the pinlike body, at least in its base region, may have a hydrophilic surface for promoting osteoblastic differentiation of mesenchymal stem cells, thereby enhancing bone formation and hence anchorage in the bone.

In the further dependent claims, further advantageous embodiments of the invention are characterized.

The invention is described in more detail below by means of working examples with reference to the drawing.

Figure 1:
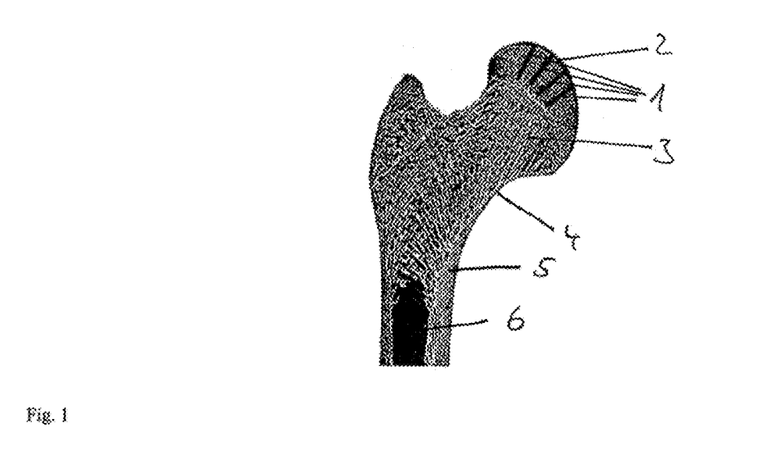
FIG. 1 shows a simplified sectional view of a femur with joint implants of the invention.

FIG. 1 shows a simplified sectional view of an upper section of a femur in order to illustrate, exemplarily, the use of the joint implants of the invention for new tissue formation at a femoral/hip joint. Represented with reference 1 in FIG. 1 are the joint implants of the invention, which can be introduced into the femur in the region of the joint. In this case, at damaged cartilage regions 2, for example, one or a multiplicity of indentations may be drilled, punched or otherwise formed in the bone, and then a respective joint implant 1 inserted into each of the indentations formed. Each indentation in this case is preferably of a size such that the joint implant 1 used, or its top region, does not protrude from the surface of the bone or cartilage 2, but instead finishes level with the latter or, preferably, the top region of the joint implant 1 lies below the surface of the bone or cartilage 2.

The articular cartilage 2, damaged as a result of joint disorder (arthritis), may be at least partly regenerated with the joint implants 1 of the invention, since at the ends and/or top regions of the joint implants 1 introduced, there is formation of new tissue and, in particular, of new articular cartilage.

According to FIG. 1, the bone has a bone-covering periosteum 4, with the end regions 3 of the bone containing a natural trabecular structure referred to as what is called spongy bone. In its central region, furthermore, the bone consists of a relatively firm bone cortex 5, and in its interior of a bone marrow cavity 6.

Through the use of an artificial trabecular structure at least on one surface of the joint implant 1, improved properties in the new formation of tissue at the joint can be achieved, as elucidated in detail below.

Figure 2A:
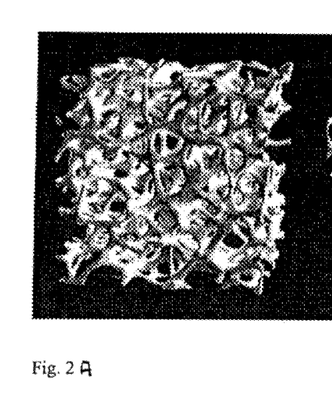
FIGS. 2A and 2B show simplified perspective views of natural trabecular structures.
Figure 2B:
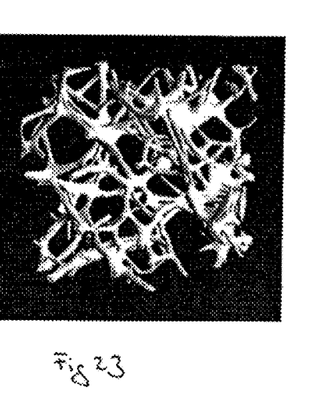

FIGS. 2A and 2B show simplified perspective views of natural trabecular structures, of the kind present, for example, in the spongy bone region 3 of the human femur. Here, according to FIG. 2A, in the case of young, healthy person, the spongy bone region 3 is interspersed by a very fine and dense natural trabecular structure, whereas, according to FIG. 2B, an older person, suffering in particular from osteoporosis, for example, often possesses a greatly altered natural trabecular structure, with only a few, very thin bone spicules (trabeculae) in the spongy bone region 3.

For example, the joint implant 1 may comprise a pinlike body which, at least on its surface or else completely, comprises an artificial trabecular structure. As a result of the artificial and at least partially open trabecular structure, or trabecular structure pervious to liquids, in the joint implant 1, for example, the possibility is created of rapid colonization of the trabecular surface, and especially of the top region of the pinlike body, by cartilage-forming cells such as chondroblasts, for example, resulting in significantly accelerated and at the same time durable overgrowth, and also enabling a high-quality regenerative cartilage.

The joint implant 1, with its artificial trabecular structure, may preferably be constructed by means of suitable 3D printing processes, and microstructured in terms of the biomedical application, in such a way that, as a result of a defined internal and external structure and roughness, there is optimum anchorage with the natural trabecular structure in the indentation (drill hole, punched indentation, etc.) in the spongy bone region 3. As a result, it is possible to rule out the vertical, lateral and, where appropriate, rotatory mobility of the joint implant 1 in the indentation.

FIGS. 3A to 3F show simplified perspective views of artificial trabecular structures according to exemplary embodiments of the present invention. The artificial trabecular structure here has a multiplicity of spicular or platelike elements (trabeculae) which combine with one another to produce a 3-dimensional microarchitecture.

In this context, the biomimetic, artificial trabeculae produced preferably by 3D printing technology ought not to undershoot or exceed certain parameters.

The parameters governing the artificial trabecular structure of the invention are defined in more detail below.

Figure 3A:
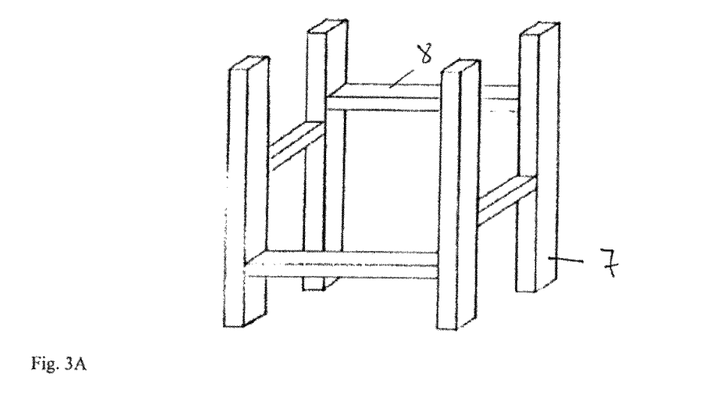
FIGS. 3A to 3F show simplified perspective views of artificial trabecular structures according to exemplary embodiments of the invention.
Figure 3B:
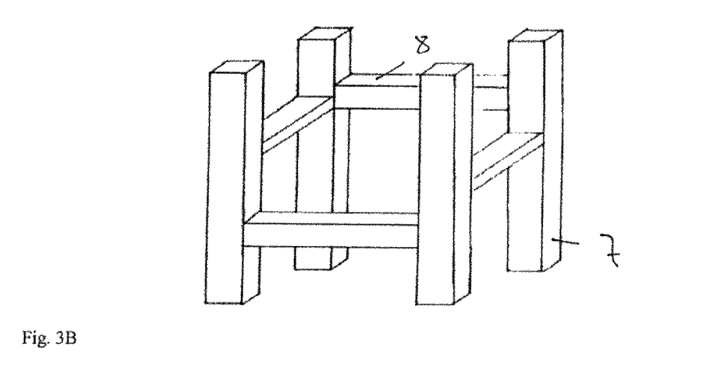

The "mean trabecular thickness" (Tb.Th) defines the average thickness of each of the trabeculae or spicular elements. Since according to FIG. 3A, for example, the respective trabeculae may have different shapes, Tb.Th represents the average of the local thicknesses of all the artificial trabeculae. The local thickness is obtained, in the case of rectangular trabeculae, for example, from the trabecular diagonal, and from the trabecular diameter in the case of circular trabeculae. FIG. 3B shows, diagrammatically, the effects on the artificial microstructure of an increase in the average trabecular thickness Tb.Th. The average trabecular thickness Tb.Th for the artificial trabecular structure is preferably in a range from 100 to 500 μm and more particularly from 150 to 400 μm.

Figure 3C:
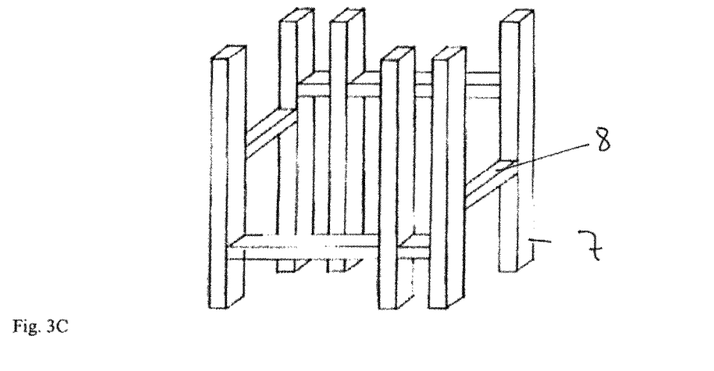
Figure 3D:
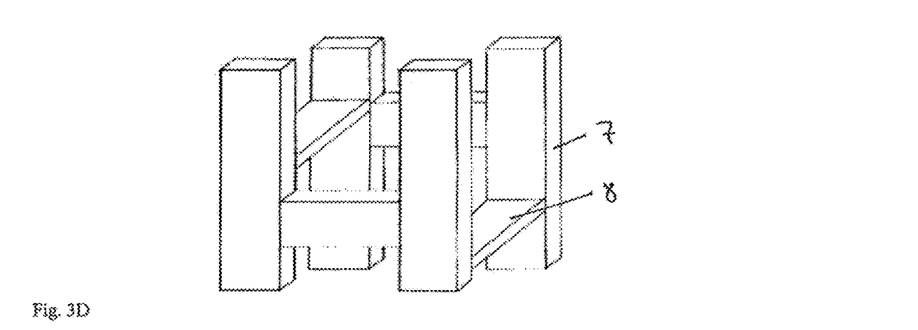

The "mean trabecular separation" (Tb.Sp) defines the average trabecular distance in analogy to the average trabecular thickness Tb.Th. A decrease in Tb.Sp may result from the changing of various other parameters, e.g. increase in Tb.Th (FIG. 3B), increase in Tb.N (FIG. 3C), or decrease in the "structure model index" SMI (FIG. 3D). The unit for the average trabecular distance Tb.Sp is μm, and for the artificial trabecular structure of the invention is situated preferably in a range between 100 μm and 900 μm and more particularly between 200 μm and 600 μm.

The "trabecular number" (Tb.N) is defined as the inverse function of the average distance between the axes of the plates and/or spicules, and indicates the number of trabeculae per mm. FIG. 3C, for example, shows an increase in Tb.N in comparison to FIG. 3A. The trabecular number Tb.N for the artificial trabecular structure is preferably in a range from 1 to 6 per mm, more particularly in a range from 1.6 to 5.2 per mm.

The "structure model index" (SMI) is a further descriptive parameter of the artificial trabecular structure, which may be, for example, a network constructed of platelike and rodlike elements. In reality, however, the trabecular network does not take on one or another form, there being instead a fluid transition. With increasing age, for example, a more platelike network becomes a more rodlike one. On the basis of this finding, therefore, the "structure model index" (SMI) was introduced, allowing the structure to be quantified in relation to the number of plates and rods. For an ideal plate model, the SMI lies at a value of 0 (i.e. pure plate structure); for an ideal rod model, it lies at a value of 3. The SMI therefore describes the relative composition of the artificial trabecular structure made up of plates and rods. FIG. 3D shows, schematically, a decrease in SMI. The SMI is dimensionless and for the present invention is for example 0.2 to 2.0, preferably 0.25 to 1.8.

Figure 3E:
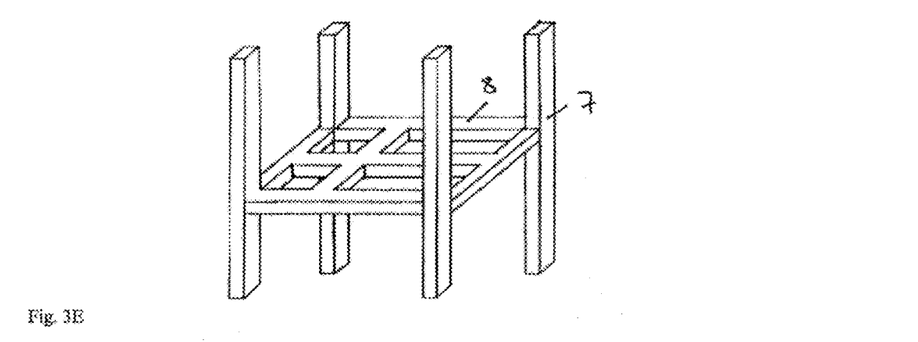

The "connectivity density" (Conn.D) is a measure of the crosslinking of the trabecular braiding. Connectivity is the maximum number of connections which within the network can be interrupted by microfractures, for example, without the net as a whole being broken down into two parts which are no longer joined to one another. FIG. 3E shows, schematically, an increase in the crosslinking density Conn.D. The crosslinking density Conn.D for the artificial trabecular structure of the invention is preferably in a range from $1/mm^3$ to $60/mm^3$, more particularly from 1.5/mm3 to 45/mm3.

Figure 3F:
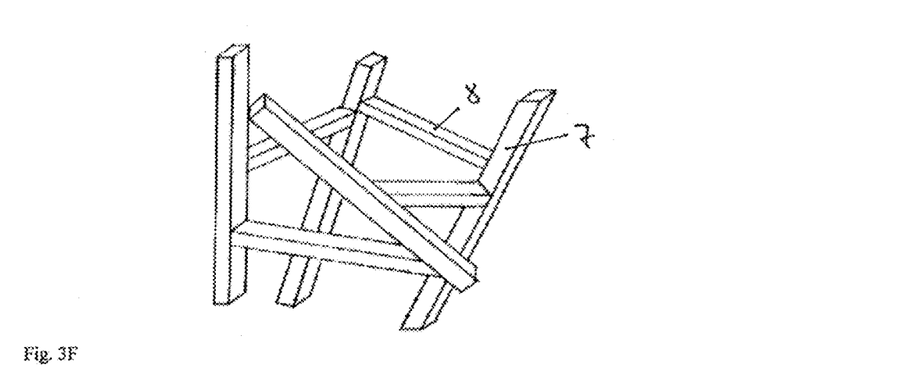

The geometric degree of anisotropy (DA) is a parameter for quantifying the spatial asymmetry. The higher the DA, the greater the extent of which there is orientation of the artificial trabecular structure in a defined direction. FIG. 3F shows, schematically, a decrease in DA. Like the parameter SMI, DA is dimensionless. A DA of 0 indicates a perfectly isotropic structure, a DA of 1 a perfectly anisotropic structure. The degree of anisotropy is also reported, supplementarily, by what is called the tDA (alternative DA), with values from 1, perfectly isotropic, to infinity, perfectly anisotropic. The tDA, however, is not used here in describing the structure according to the invention. The geometric degree of anisotropy DA for the artificial trabecular structure of the invention is preferably in a range from 0.1 to 1.0, more particularly from 0.2 to 0.8, and with further preference is 0.2 to 0.6.

The "bone volume tissue volume fraction" (BV/TV) is the volumetric fraction of the trabeculae as a proportion of the total volume of a trabecular structure under consideration. An increase in BV/TV may result from a change in various other parameters, e.g. increase in Tb.Th (FIG. 3B), increase in Tb.N (FIG. 3C) or decrease in SMI (FIG. 3D). For the trabecular structure of the invention, BV/TV is preferably in a range from 6% to 70%, more preferably from 20 to 50%.

Lastly, the "marrow star volume" (MSV) defines a particular trabecular porosity of the artificial trabecular structure. More precisely, the MSV defines the size of the cavities in the artificial trabecular structure. The arithmetic mean mMSV in accordance with the invention is preferably in a range from 0.05 $mm^3$ to 110 $mm^3$, more particularly between 0.05 $mm^3$ to 9 $mm^3$, and with further preference between 0.05 $mm^3$ to 5 $mm^3$.

Figure 4:
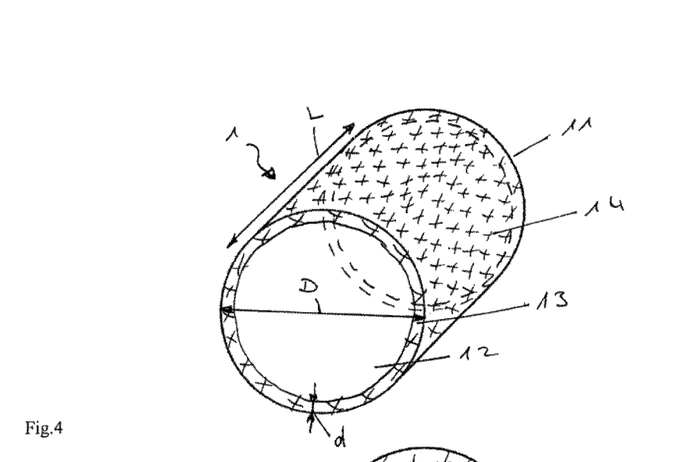
FIG. 4 shows a simplified perspective view of a joint implant according to a first exemplary embodiment of the invention.

FIG. 4 shows a simplified perspective view of the joint implant 1 according to a first exemplary embodiment of the invention. The joint implant 1 here comprises a pinlike body in the form of a solid cylinder (impervious to liquid), which has a bottom region 11, a shell region 13 and a top region 12. The joint implant 1 here can be inserted into the bone, in accordance with FIG. 1, in such a way that its top region 12 in the region of the cartilage 2 is disposed preferably with a slight indentation in the bone.

Accordingly, the top region 12 of the joint implant 1 is able to act as a growth region for the newly forming tissue or the newly forming articular cartilage 2. The bottom region 11 and also the lower part of the joint implant are preferably located wholly or partly in the spongy bone region 3.

According to FIG. 4, the above-described artificial trabecular structure 14 may be formed at least in a shell region 13. Furthermore, however, the top region 12, in particular, may also have the artificial trabecular structure 14. As a result of the open trabecular structure of the joint implant 1, which is pervious to bodily fluids, for example, rapid colonization of the trabecular surface with cells such as chondroblasts is enabled, resulting in significantly accelerated overgrowth. Furthermore, depending on structure and coating, the joint implant of the invention allows the growth of a regenerative fibrocartilage up to a high-grade, hyalin regenerative cartilage, in particular on the top region 12.

The pinlike body of the joint implant 1 preferably has a length L of at least 0.6 cm and at most 1.2 cm for patellar application and application in small joints such as, for example, the wrist or ankle joint, and at least 0.8 cm and at most 2.2 cm, more particularly 1.0 cm to 1.6 cm, and with further preference 1.25 cm, for respective proximal and distal, tibial and femoral application in the knee and hip joints. As a result, an optimum of accessibility and ingrowth of mesenchymal stem cells can be made possible. The pinlike body of the joint implant 1 may further have a diameter D of at least 2 mm and at most 6 mm, preferably 3 mm, so enabling an optimum of lateral surface, facing the synovia, to be achieved, for the purpose of forming replacement cartilage tissue. A thickness d of the artificial trabecular structure 14 (e.g. of the shell region 13) is preferably 0.5 to 2.0 mm, more preferably 0.5 to 1.5 mm.

By means of a defined, repetitive network structure, based on the natural trabecular structure, of the artificial trabecular structure, or a channel structure with appropriately adapted form of the joint implant 1, or a combination of network structure and channel structure, it is possible to enable optimum ingrowth of endogenous tissue into the boundary volume between joint implant 1 and indentation or drilled channel, especially into the internal volume of the shell region 13 of the joint implant 1, and above that end of the joint implant 1 that points to the synovia (joint cavity).

The joint implants 1, as microstructured pins, are formed preferably on the basis of medically approved, bioinert and biocompatible, 3D-printable materials such as, for example, non-bioabsorbable polymers, more particularly polyamide (PA), polyetherketones, more particularly PEK [polyetherketone], PEKK [poly(etherketoneketone)], PEEK [polyetheretherketone], polyethylene (PE), more particularly UHMWPE [ultra-high molecular weight polyethylene], or, for example, bioabsorbable polymers, more particularly PCL [poly-ε-caprolactone].

Alternatively, preferably 3D-print-suitable metals and metal alloys, more particularly titanium (grade 1 pure titanium), especially Ti64 (Ti6Al4V), Ti64 ELI and TiCP, stainless steel, especially 316L, and cobalt-chromium alloys, especially CoCr, can also be used as materials for the joint implants 1, and in particular for their artificial trabecular structures.

It is also possible, furthermore, for non-bioabsorbable, preferably 3D-print-suitable, ceramics, especially aluminum oxide ceramic [Al2O3], and zirconium dioxide ceramic [ZrO2], or bioabsorbable ceramics, especially calcium phosphate ceramic [Ca3(PO4)2], to be used as materials for the joint implants 1.

In principle it is also possible for further medically approved, bioinert and biocompatible materials, and especially 3D-printable materials, to be used for the joint implants 1 and, in particular, for the artificial trabecular structures 14 according to FIGS. 3A to 3F.

Figure 5:
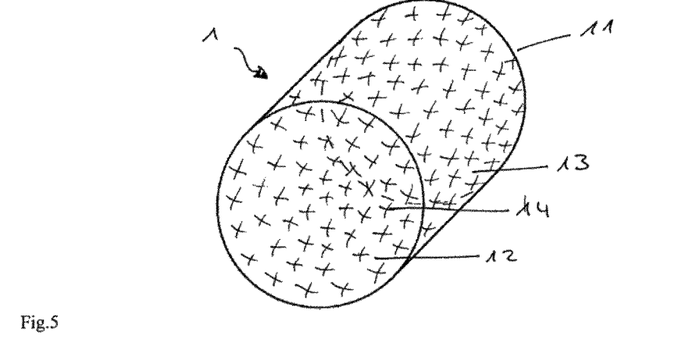
FIG. 5 shows a simplified perspective view of a joint implant according to a further exemplary embodiment of the invention.

FIG. 5 shows a simplified perspective view of the pinlike body of the joint implant 1 according to a further exemplary embodiment of the invention, with identical reference symbols denoting identical or corresponding elements, which are therefore not described again below. Whereas, according to FIG. 4, the pinlike body of the joint implant 1 may comprise a solid cylinder, with the trabecular structure 14 of the invention formed at least on its lateral surface, the pinlike body of the joint implant 1 according to FIG. 5 may also consist entirely of the artificial trabecular structure 14. This allows a further improvement to be achieved in the inflow, proliferation and migration of fibrocytes, mesenchymal stem cells and chondroblasts from the spongy bone region 3 into the cartilage defect.

Figure 6:
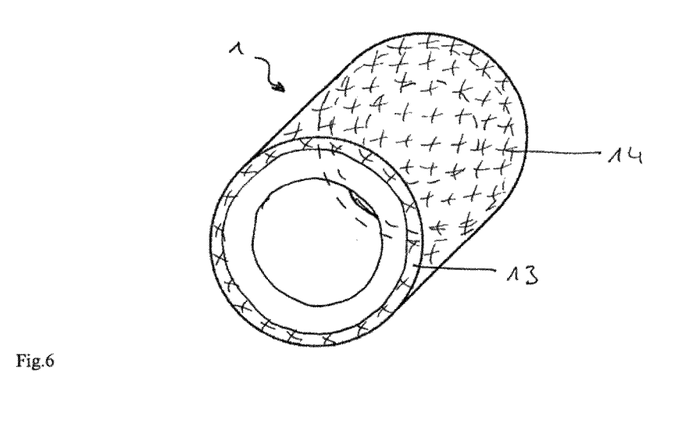
FIG. 6 shows a simplified perspective view of a joint implant according to a further exemplary embodiment of the invention.

FIG. 6 shows a simplified perspective view of the pinlike body of the joint implant 1 according to a further exemplary embodiment of the invention, with identical reference symbols denoting identical or corresponding elements, which are therefore not described again below. According to FIG. 6, the pinlike body of the joint implant 1 may preferably comprise a hollow body, such as hollow cylinder, for example, in which case the artificial trabecular structure 14 is formed at least in a shell region 13 of the hollow cylinder. For example, the hollow body has at least one coherent cavity or a plurality of non-coherent cavities. Alternatively, however, the hollow cylinder may also consist completely of the artificial trabecular structure 14 (not shown). The inflow, the proliferation and the migration of fibrocytes, mesenchymal stem cells and chondroblasts from the spongy bone region 3 into the cartilage defect may be improved further through this enlargement of the interaction surface.

Figure 7:
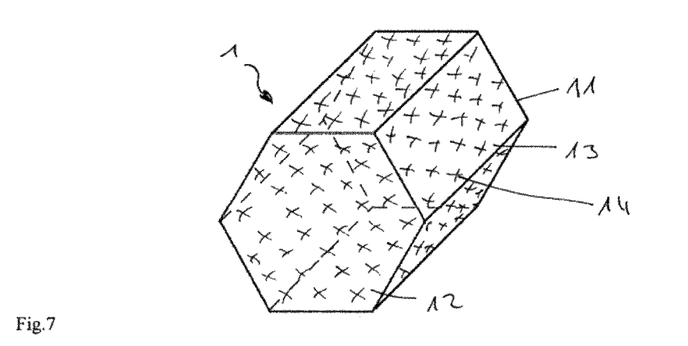
FIG. 7 shows a simplified perspective view of a joint implant according to a further exemplary embodiment of the invention.

FIG. 7 shows a simplified perspective view of the joint implant 1 according to a further exemplary embodiment of the invention, with identical reference symbols denoting identical or corresponding elements, which is why they are not described again below. According to FIG. 7, the pinlike body of the joint implant 1 may also have the form of a prism or hollow prism (not shown). As a result of the macrostructuring, in the form of a polygonal cross section, for example, a further improvement is achieved in anchoring of the joint implant in the bone or spongy bone region 3, thus further improving the long-term integrity of the joint implants.

Figure 8:
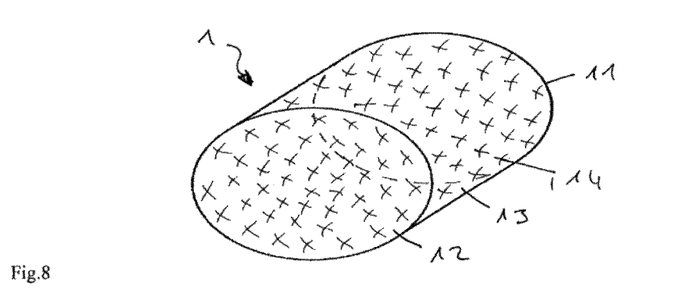
FIG. 8 shows a simplified perspective view of a joint implant according to a further exemplary embodiment of the invention.

FIG. 8 shows a simplified perspective view of the pinlike body of the joint implant 1 according to a further exemplary embodiment of the invention, with identical reference symbols denoting identical or corresponding elements, which is why they are not described again below. Alternatively, according to FIG. 8, the joint implant 1 used may also be a hollow body or body which is cross-sectionally ellipsoidal, in which case, in turn, improved anchoring and, in particular, reduced rotatory mobility about the longitudinal axis are anticipated, but the incidence of unwanted fracture segments at edges and corners is reduced. As a result, long-term integrity is further enhanced.

Figure 9:
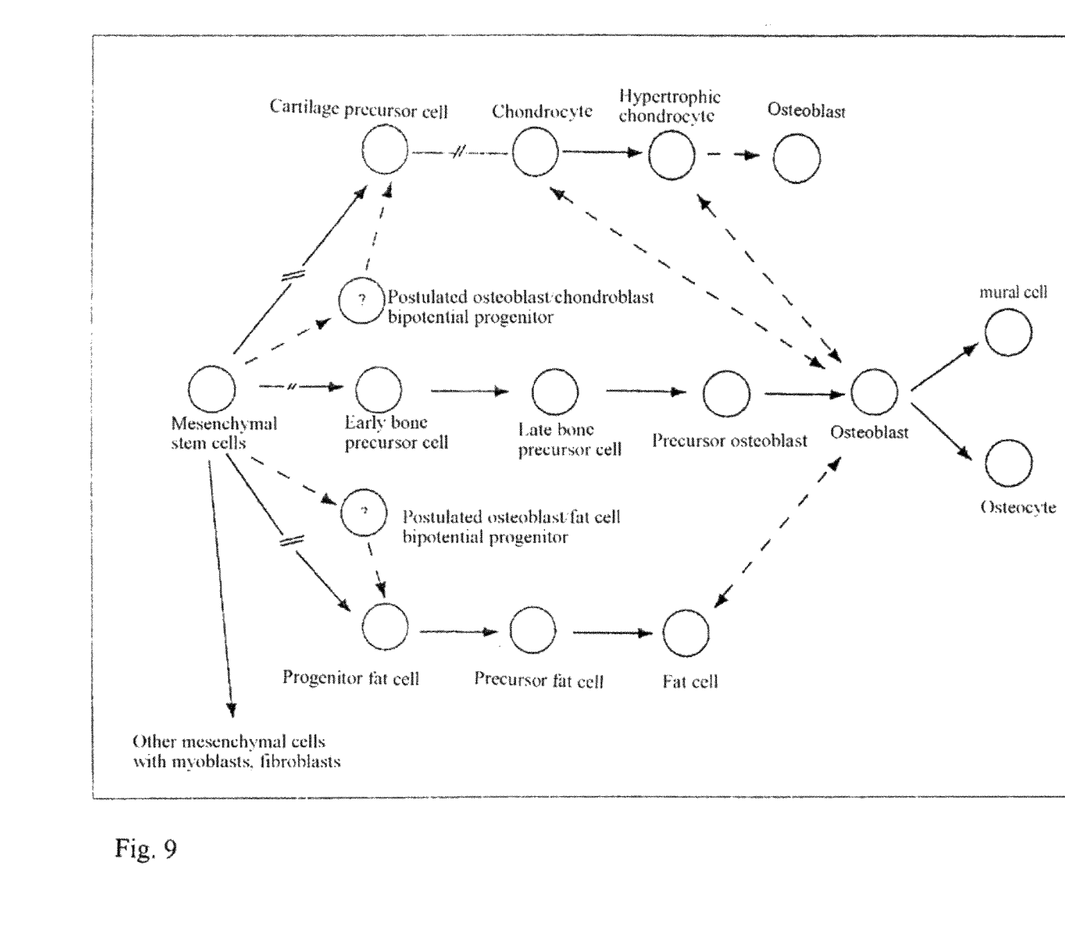
FIG. 9 shows a schematic overview of the various maturation stages of mesenchymal stem cells, after Aubin 1998.

FIG. 9 shows a schematic overview of the various stages of maturation of mesenchymal stem cells, after Aubin, 1998. In accordance with the invention it is desirable for mesenchymal stem cells (MSCs) to differentiate, at least in the top region 12 of the pinlike body of the joint implant 1, into chondrocytes, in order to generate the formation of new cartilage desired in this region. Conversely, in the lower part or bottom region 11 of the pinlike body of the joint implant 1, differentiation of the mesenchymal stem cells (MSCs) into osteocytes may be advantageous, in order to promote bone formation and hence optimum growth of the joint implant 1 into the spongy bone region 3.

Surprisingly it has been found that this kind of differentiation of mesenchymal stem cells may be promoted simply by the generation of a corresponding substrate. To put it more precisely, it was possible to observe that a hydrophobic surface of a substrate promotes chondroblastic differentiation of mesenchymal stem cells and therefore formation of cartilage, whereas a hydrophilic surface of a substrate or base promotes osteoblastic differentiation of mesenchymal stem cells and therefore formation of bone.

The terms "hydrophobicity" or "hydrophobic surface", and "hydrophilicity" or "hydrophilic surface", are defined below by way of what is called the contact angle of a water droplet on a surface. In this regime, hydrophobic surfaces have a contact angle of greater than or equal to 90°, while contact angles of greater than 160° are characteristic of superhydrophobic surfaces. The best-known representative of these superhydrophobic surfaces is the plant known as the "lotus" plant, which by virtue of its particular microstructuring and nanostructuring exhibits contact angles of up to 170°. On the other hand, hydrophilic surfaces are characterized by a contact angle of less than 90°.

In accordance with the invention, then, this capacity of the stem cells for differentiation depending on the hydrophobicity or hydrophilicity of a surface is exploited by the pinlike body of the joint implant 1 having corresponding hydrophobic surfaces which promote chondroblastic differentiation of the mesenchymal stem cells and therefore development of cartilage.

In this context, either the entire pinlike body may have a hydrophobic surface, or else only part of the body may possess hydrophobic surfaces. For example, at least the top region 12 has a hydrophobic surface, in order to promote cartilage growth at this point. On the other hand, the pinlike body may have a hydrophobic surface in its top region 12 and upper shell region 13, while the bottom region 11 and the lower part of the shell region 13 have a hydrophilic surface. As a result, cartilage growth can be promoted in the upper region (the region protruding from the bone) of the joint implant 1, and bone growth can be promoted in the lower region (the region located in the bone) of the joint implant.

In accordance with the invention, the hydrophobic surface, and hence a surface promoting chondroblastic differentiation, may be realized in a variety of different ways. On the one hand, chemical coatings may be applied to the pinlike body and especially to its trabecular structures, these coatings enhancing the hydrophobic (water repelling) properties. On the other hand, suitable microstructuring and/or nanostructuring of the surface of the pinlike body, and especially its trabecular structures, may also bring about a desired hydrophobic quality. Furthermore, combinations of such hydrophobic chemical coatings with physical topographical structuring (microstructuring and/or nanostructuring) may also be used in order to realize such "lotus effect" surfaces with hydrophobic qualities, in order to promote chondroblastic differentiation and hence the growth of cartilage.

Figure 10A:
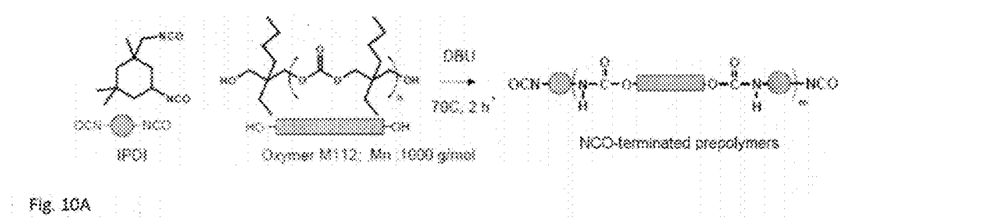
FIGS. 10A and 10B show an exemplary embodiment for the production of a hydrophobic chemical coating, using segmented polyurethanes as an example.
Figure 10B:
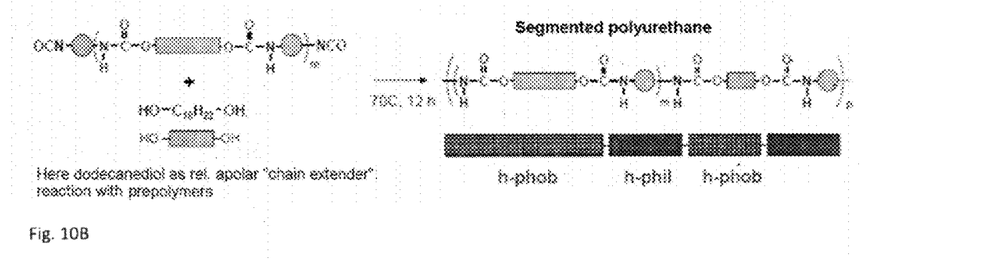

FIGS. 10A and 10B show an exemplary embodiment of the production of a hydrophobic coating of this kind, using the example of segmented polyurethanes, as may be applied to a joint implant of the invention.

According to FIG. 10A, the preparation of NCO-terminated prepolymers is illustrated first of all, there being a stoichiometric excess of —NCO. According to FIG. 10B, subsequently, the NCO-terminated prepolymers are converted, using dodecanediol as apolar "chain extender", into the desired segmented polyurethane (segmented PU).

Figure 11A:
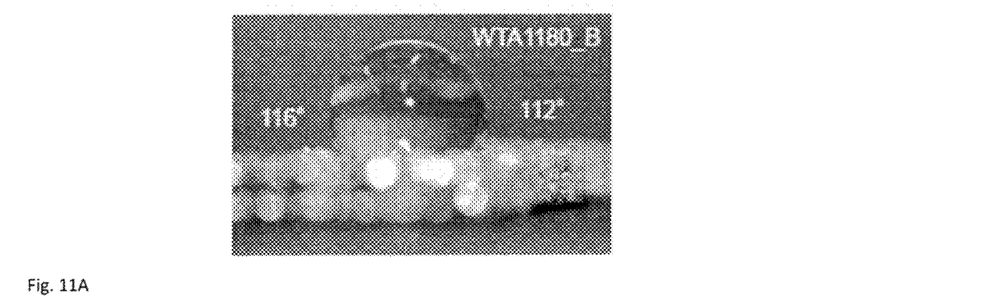
FIGS. 11A and 11B show enlarged views of Ti substrates, coated with segmented PU, for illustration of a respective contact angle.

FIG. 11A shows an enlarged view of a Ti substrate coated with a segmented PU of this kind. Whereas an uncoated Ti substrate (not shown) has a contact angle of 0°, the Ti surface coated with segmented PU (10% PU in toluene) possesses a contact angle of approximately 112° to 116°.

Figure 11B:
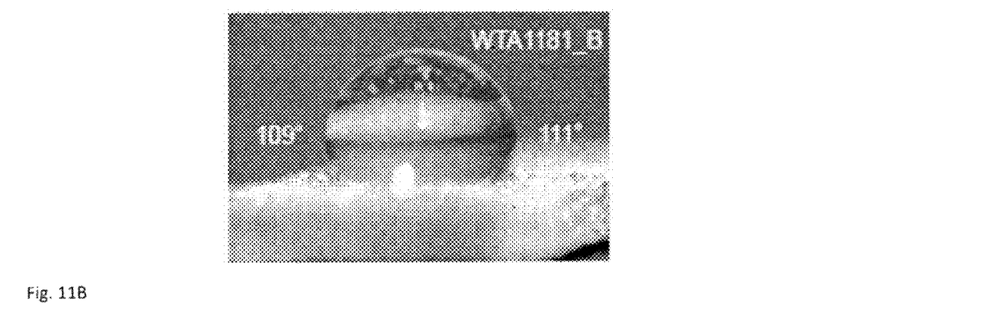
Figure 12A:
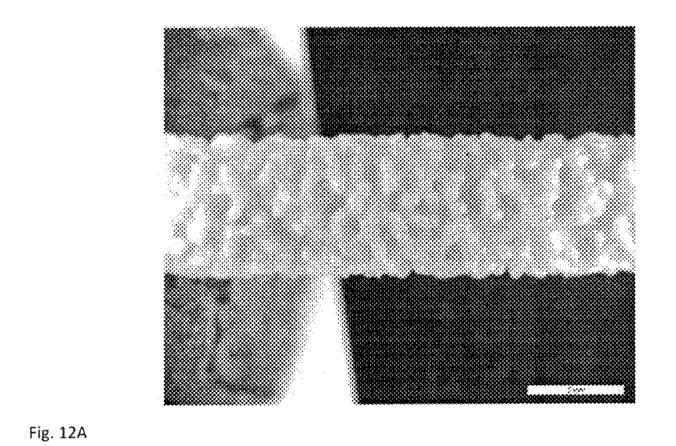
FIGS. 12A and 12B show a perspective view and also a partially enlarged view of the pinlike body of the joint implant according to a further exemplary embodiment of the invention.
Figure 12B:
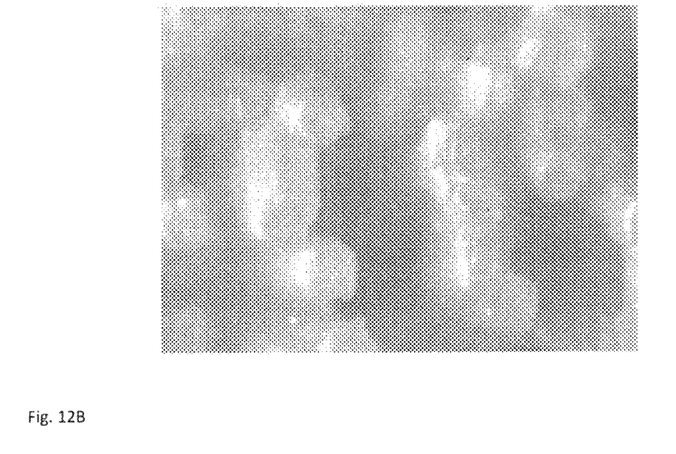

FIG. 11B shows an enlarged view of a Ti substrate coated with a segmented PU, the concentration of the segmented PU being 2% in toluene. The Ti surface coated with a segmented PU of this kind now has a contact angle of approximately 109° to 111°.

For the hydrophobic PU coating described above, the components used were as follows:

a) aliphatic diisocyanates: isophorone diisocyanate (IPDI), hexamethylene diisocyanate (HDI) and dicyclohexylmethane diisocyanate (hydrogenated MDI, HMDI)

b) polyols: polycarbonate diols (hydrolysis stability), such as e.g. Desmophen C2200, Desmophen XP2586, and also hydrocarbon diols based on natural rubber and hydrogenated natural rubber c) chain extenders: aliphatic diols such as hexanediol, decanediol and possibly longer diols on account of the hydrophobicity As a hydrophobic chemical coating it is also possible, furthermore, to use a PU-based polyelectrolyte complex. In this case the same components as above are used, with sulphonated diols, or diols containing ammonium groups, being used additionally as chain extenders in order to introduce ionic groups for the formation of the electrolyte complexes. Complexing is then accomplished after coating (preferably dip coating) by immersion into a dilute solution containing a surfactant (cationic or anionic, according to the ionic groups present in the polymer). The ionic interactions between the polyelectrolyte and the surfactant result in a firm bond, particularly if the surfactant is hydrophobic and therefore in any case has no tendency in an aqueous environment to enter into solution.

As a hydrophobic chemical coating it is also possible, furthermore, to use an acrylate-based polyelectrolyte complex, in which case a first layer of polyelectrolytes such as polyacrylic acid and/or acrylic- or methacrylic-acid-containing copolymers, possibly also with some phosphoric acid groups (vinylphosphonic acid as comonomer), is applied to the surface for adhesion, after which a second layer is applied as above (coating from a surfactant solution, tailored to the ionic groups of the polyelectrolyte).

Preference is given to using the following three types of hydrophobic coating materials:
polyurethane crosslinked
polyurethane uncrosslinked
polyelectrolyte complexes
which have the following characteristics:
Polyurethane Crosslinked:

Polyurethanes differ from the majority of other polymers and plastics in that they are composed by means of a "building block system" of a large number of different components (diisocyanates, polyisocyanates, polyols, chain extenders, soft segments, etc.). The actual construction here (chemical synthesis of the polymer molecules) is typically accomplished not until during processing, and so the user and/or producer of components is able to assemble the ultimate properties, on the basis of polyurethanes, entirely according to his or her requirements. Virtually all other plastics, in contrast, are produced with set profiles of properties by the raw materials manufacturer (chemical industry) and dispatched in that form, meaning that the user and/or producer of components has only relatively little influence over the profile of properties. Polyurethanes therefore represent a very good starting basis for specialty developments such as the coating of the implant body 1 of the invention.

Polyurethanes have long been used as biocompatible materials, for example as inert, non-degradable coatings on cardiac pacemakers, or else as biocompatible, degradable support materials (scaffolds) for tissue engineering and/or regenerative medicine. The properties (e.g. hydrophobicity/hydrophilicity, degradability/long-term stability, strength, stiffness, porosity, etc.) here are adjusted as required through the combination of the components.

Crosslinked polyurethanes are prepared in dilute solution in the presence of the substrate to be coated. In this case the components can be selected so that crosslinking is at the same time accompanied by chemical attachment to the surface of the substrate to be coated. These materials often exhibit outstanding adhesion, particularly to hydrophilic surfaces, without adhesion promoters or similar intermediate coats. The components of the polyurethanes can be selected so that the resultant coats are themselves hydrophobic.

For the biocompatibility, suitable components are aliphatic di- and polyisocyanates; for the long-term stability, soft segments and polycarbonate-, silicone- or polybutadiene-based polyols; and, for the hydrophobicity, long-chain diols, possibly likewise silicone-based or polybutadiene-based, as chain extenders.

The main disadvantage is the problem controlling the coat thickness in the course of coating. The concentration is the only independent parameter which can be varied in order to influence the coat thickness. While the composition and the reaction time do affect the coat thickness, the composition, nevertheless, also influences all of the other properties, and the reaction time cannot be set arbitrarily, since biocompatibility requires the complete conversion of the isocyanate groups, and so the coating time cannot be shortened ad infinitum.

Polyurethanes, Uncrosslinked:

Uncrosslinked polyurethanes are prepared separately from the coating operation and are subsequently applied from a dilute solution in a dipping operation. The adjustment of the properties offers the same opportunities as in the case of the crosslinked polyurethanes, since virtually all components can be used in both cases.

The advantage of the uncrosslinked polyurethanes is that synthesis and coating proceed separately from one another, and so there are better opportunities for controlling the coat thickness. The concentration, the exposure time during the dipping operation, and, in particular, the number of dipping operations (with drying between in each case) determine the thickness of the applied coat.

The disadvantage is that chemical attachment of the coat to the substrate requires either a layer of adhesion promoter, or specific components in the polyurethane which are able to react with the surface. In certain circumstances, therefore, the adhesion of these coats is less long-lasting, or the coating operation is more costly and inconvenient, requiring the application, first, of a layer of adhesion promoter ahead of the actual coating procedure. Since, however, provisionally an adhesion promoter coat can likewise be applied simply by dip coating, the additional cost and complexity are limited.

Polyelectrolyte Complexes:

Polyelectrolyte complexes exploit electrostatic interactions between positively and negatively charged ions and surfaces. Every material, in water, exhibits a certain surface charge (zeta potential), which is positive or negative, according to the chemical structure. This surface charge is also possessed by neutral particles or surfaces. Polyelectrolytes whose charges along the polymer chain carry an opposite charge to this surface charge adhere very firmly to the surface. In general they can no longer be removed, since each polymer chain, according to chain length, adheres simultaneously with dozens or hundreds of groups and so is maintained in position even when some of these groups are detached by external exposures. In one case, polyelectrolytes of opposite charge can then be deposited on the first polyelectrolytes, thereby enabling precise establishment of the coat thickness on a molecular basis, by means of alternate deposition (layer-by-layer technique). Alternatively, ions of low molecular mass, such as surfactants or soaps, are deposited, with one end of these molecules carrying a charge opposite to that of the polyelectrolyte, in order to ensure the adhesion, while their other end is hydrophobic. In this way, ideally, coats can be produced which to the outside have a dense layer of, for example, methyl groups, so making it possible to achieve virtually the surface tension of fluoropolymers (PTFE, Teflon).

The advantages of these materials lie in the usually outstanding adhesion in aqueous or non-aqueous systems, in the precise controllability of the coat thickness, and in the relatively well-controllable, highly pronounced hydrophobicity.

A disadvantage is the deposition in virtually monomolecular layers, which in case of higher coat thicknesses necessitates a large number of dipping operations in alternating polyelectrolyte baths. Since, however, no intermediate drying steps are needed, the cost and complexity are acceptable.

As starting material for the pinlike body of the joint implant 1, it is additionally possible to use such 3D-printable materials which already per se (that is, without additional microstructuring and/or nanostructuring and chemical coating) have a hydrophobic surface. For example, the untreated surface of a zirconium dioxide ceramic substrate already exhibits hydrophobic properties.

Alternatively or additionally to the above-described hydrophobic chemical coating or selection of materials, it is possible, furthermore, to generate micro- and nanostructured surfaces on the pinlike body of the joint implant 1, of the kind also known, as self-cleaning surfaces, under the term Lotus Effect®. Micro- and nanostructured surfaces of this kind are known from publication WO 96/04123 A, for example.

Furthermore, the artificial trabecular structures 14 may have an additional growth coating and/or a growth factor for the purpose of improved cartilage cell differentiation and improved attachment of cartilage material. The artificial trabecular structure 14 may preferably be coated with specific, human and human-homologous growth factor FGF [Fibroblast Growth Factor], particularly FGF-1, FGF-2 and FGF-10 to FGF-22, and among the latter particularly FGF-18. Alternatively, the artificial trabecular structure 14 may be coated with specific, human and human-homologous growth factor SDF [Stromal Cell-Derived Factor], especially SDF-1. Furthermore, specific, human and human-homologous growth factor IGF-1 [Insulin-like Growth Factor 1], human PDGF [Platelet-Derived Growth Factor], specific, human and human-homologous growth factor TGF-β1 and TGF-β3 [Transforming Growth Factors beta 1 and beta 3], or specific, human and human-homologous BMP-2 and BMP-7 [Bone Morphogenetic Protein-2 and Protein-7] may be applied to the artificial trabecular structure 14. Further coating possibilities include the following: specific, human and human-homologous OP-1 [Osteogenic Protein-1], human PRP [Platelet-rich Plasma], and also bioinert polyamide suitable especially for coatings. Also possible, of course, are combinations of the coatings described above. With preference the growth factor may be applied as the last coat.

In accordance with the invention, through appropriate selection of suitable bioinert and biocompatible materials with ideal adaptation of the geometrical and chemical/biochemical surface structure (artificial trabecular structure), the differentiation of mesenchymal stem cells into chondroblasts or osteoblasts can be controlled in a targeted way. As a result, in particular, it is possible to improve the cartilage structure on the synovia-facing side (top region 12) of the joint implants 1, by means of the above-described hydrophobic surface structures and coatings, and also with the growth factors which stimulate cartilage formation. Moreover, on the synovia-remote side (bottom region 11) of the joint implants, hydrophilic surface structures and coatings can be used to improve bone formation and also the bone structure in the spongiose bone region. This produces almost physiological suitability, because the joint anatomy and the natural bone stability are influenced not at all or only insignificantly as in the case, for example, of implantation of an endoprosthesis. The compatibility and activity of the curative therapy by means of the above-described joint implants are substantially enhanced as a result.

Through the combination of the above-described biocompatible, bioinert, 3D-printable materials, the specifically suitable biomedical geometries (curvature, nanostructure, microstructure and macrostructure) and the growth-promoting coatings, an innovative joint implant is obtained which is able to optimize further the quantity and quality and hence the robustness and integrity of replacement cartilage tissue, and to make a key contribution to the curative treatment of joint disorders (arthritis).

The invention has been described above using preferred exemplary embodiments. However, it is not confined to these embodiments, and in particular it also encompasses individual combinations of the above-described exemplary embodiments. In particular, carbon as well can be used as material for the joint implants, and particularly for the artificial trabecular structures.

Although the invention has been described above in connection with use in human hip and knee joints, it is not confined to these applications, and in particular it also encompasses small and very small human joints (e.g. foot and finger joints), and joints of animals.

LIST OF REFERENCE SYMBOLS

1 Joint implant
2 Articular cartilage
3 Spongy bone region
4 Periosteum
5 Bone cortex
6 Bone marrow cavity
7, 8 Trabeculae
11 Bottom region
12 Top region
13 Shell region
14 Artificial trabecular structure
D Diameter of the joint implant
L Length of the joint implant
d Thickness of the artificial trabecular structure

The invention claimed is:

1. Joint implant that forms new tissue at a joint, the joint implant (1) comprising a pinlike body comprising an elongated solid that is impervious to liquid, wherein the elongated solid has a non-porous interior, a bottom region (11), a top region (12) and a shell region (13), characterized in that: at least the top region (12) and the shell region (13) of the elongated solid comprise a hydrophobic surface that promotes chondroblastic differentiation of mesenchymal stem cells, wherein an artificial trabecular structure (14) extends radially outward from the side of the pinlike body; and the bottom region (11) includes a hydrophilic surface that promotes bone growth.

2. Joint implant according to claim 1, characterized in that the artificial trabecular structure (14) is produced by means of a 3D printing process.

3. Joint implant according to claim 1, characterized in that the elongated solid constitutes a hollow body having at least one or more cavities.

4. Joint implant according to claim 1, characterized in that the elongated solid has the form of a cylinder, ellipsoid or prism.

5. Joint implant according to claim 1, characterized in that the material of the pinlike body comprises a polymer of at least one of PA, PEK, PEKK, PEEK, UHMWPE or PCL.

6. Joint implant according to claim 1, characterized in that the material of the pinlike body comprises a metal from at least one of Ti, stainless steel, or a metal alloy of at least one of Ti64 or CoCr.

7. Joint implant according to claim 1, characterized in that the material of the pinlike body comprises a ceramic of at least one of $Al_2O_3$, $ZrO_2$ or $Ca_3(PO_4)_2$.

8. Joint implant according to claim 1, characterized in that the hydrophobic surface is realized through a hydrophobic chemical coating.

9. Joint implant according to claim 8, characterized in that the hydrophobic chemical coating comprises a segmented polyurethane or polyelectrolyte or a hydrophobically functionalized chitosan or chitosan derivative.

10. Joint implant according to claim 1, characterized in that the hydrophobic surface comprises a plurality of contact angles greater than 90 degrees.

11. Joint implant according to claim 1, characterized in that the pinlike body of the joint implant (1) has a length (L) of 0.6 cm to 2.2 cm.

12. Joint implant according to claim 1, characterized in that the pinlike body of the joint implant (1) has a diameter (D) of 2 mm to 6 mm.

13. Joint implant according to claim 1, characterized in that at least the top region (12) of the joint implant (1) has a growth factor for promoting chondroblastic differentiation of mesenchymal stem cells.

14. Joint implant according to claim 1, characterized in that at least the bottom region (11) of the joint implant (1) has a hydrophilic surface for promoting osteoblastic differentiation of mesenchymal stem cells.

15. Joint implant according to claim 1, wherein the artificial trabecular structure (14) is coated with at least one of: FGF-1, FGF-2, FGF-10 to FGF-22, SDF-1, IGF-1, PDGF, TGF-β1 and TGF-β3, BMP-2 and BMP-7, OP-1, PRP, or bioinert polyamide.

16. Joint implant according to claim 1, wherein the trabecular structure is defined on a lateral surface of the elongated solid.

17. Joint implant according to claim 1, wherein the artificial trabecular structure (14) extends radially outward from the side of the pinlike body at the top region (12) and the shell region (13).

* * * * *